(12) United States Patent
Serhan et al.

(10) Patent No.: US 7,320,686 B2
(45) Date of Patent: Jan. 22, 2008

(54) DEVICE FOR DISTRACTING VERTEBRAE AND DELIVERING A FLOWABLE MATERIAL INTO A DISC SPACE

(75) Inventors: Hassan Serhan, South Easton, MA (US); Michael Slivka, Taunton, MA (US)

(73) Assignee: Depuy Acromed, Inc., Raynham, MA (US)

( * ) Notice: Subject to any disclaimer, the term of this patent is extended or adjusted under 35 U.S.C. 154(b) by 666 days.

(21) Appl. No.: 10/267,612

(22) Filed: Oct. 9, 2002

(65) Prior Publication Data

US 2004/0073213 A1   Apr. 15, 2004

(51) Int. Cl.
*A61B 17/58* (2006.01)
*A61F 2/00* (2006.01)

(52) U.S. Cl. ........................................................ 606/90
(58) Field of Classification Search .................. 606/90, 606/57, 92, 105, 63, 93, 94
See application file for complete search history.

(56) References Cited

U.S. PATENT DOCUMENTS

| | | | | |
|---|---|---|---|---|
| 4,492,576 A | * | 1/1985 | Dragan | 433/90 |
| 4,772,287 A | | 9/1988 | Ray et al. | |
| 5,562,736 A | | 10/1996 | Ray et al. | |
| 5,645,597 A | | 7/1997 | Krapiva | |
| 5,720,726 A | * | 2/1998 | Marcadis et al. | 604/103.08 |
| 5,752,969 A | * | 5/1998 | Cunci et al. | 606/167 |
| 5,762,629 A | * | 6/1998 | Kambin | 604/164.11 |
| 5,968,062 A | * | 10/1999 | Thomas et al. | 606/180 |
| 6,039,761 A | | 3/2000 | Li | |
| 6,135,999 A | * | 10/2000 | Fanton et al. | 606/45 |
| 6,159,215 A | | 12/2000 | Urbahns | |
| 6,174,311 B1 | * | 1/2001 | Branch et al. | 606/61 |
| 6,187,048 B1 | | 2/2001 | Milner et al. | |
| 6,224,599 B1 | * | 5/2001 | Baynham et al. | 606/61 |
| 6,248,131 B1 | | 6/2001 | Felt et al. | |
| 6,264,659 B1 | | 7/2001 | Ross et al. | |
| 6,395,007 B1 | * | 5/2002 | Bhatnagar et al. | 606/94 |
| 6,443,988 B2 | * | 9/2002 | Felt et al. | 623/17.12 |
| 6,488,667 B1 | * | 12/2002 | Murphy | 604/272 |
| 6,558,390 B2 | * | 5/2003 | Cragg | 606/80 |
| 6,613,018 B2 | * | 9/2003 | Bagga et al. | 604/187 |
| 6,780,192 B2 | * | 8/2004 | McKay et al. | 606/99 |
| 7,004,945 B2 | * | 2/2006 | Boyd et al. | 606/92 |
| 7,014,633 B2 | * | 3/2006 | Cragg | 604/500 |
| 2002/0077701 A1 | | 6/2002 | Kuslich | |
| 2004/0059339 A1 | * | 3/2004 | Roehm et al. | 606/90 |
| 2004/0106999 A1 | * | 6/2004 | Mathews | 623/17.16 |

FOREIGN PATENT DOCUMENTS

EP        0646366 A      4/1995

OTHER PUBLICATIONS

European Search Report EP 03256344 dated Jan. 13, 2004.

* cited by examiner

*Primary Examiner*—Anuradha Ramana

(57) ABSTRACT

The present invention provides a device for distracting two vertebral bodies and delivering a flowable material into the disc space, comprising a body having a proximal portion and a distal portion, the distal portion having a shape adapted to distract, the body also having a longitudinal bore defining a first outlet port in the distal portion, and a first injection port in the proximal portion.

15 Claims, 3 Drawing Sheets

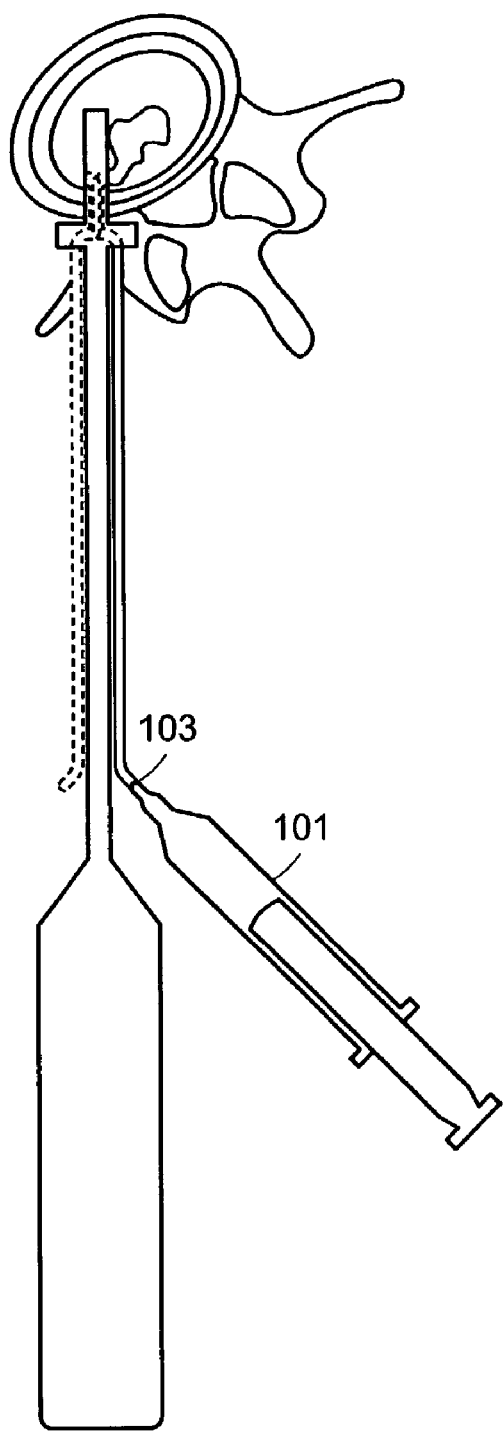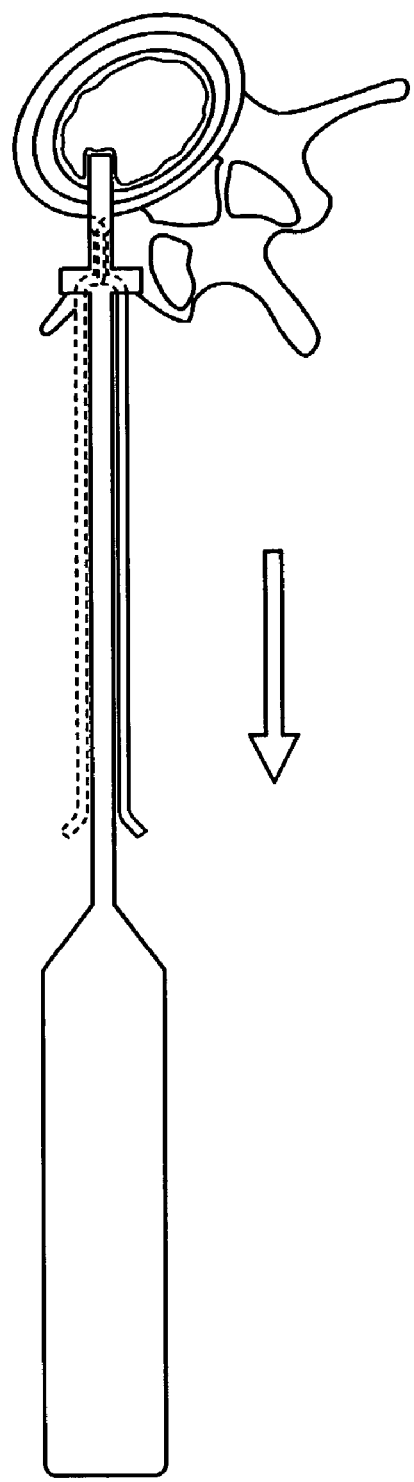
FIG. 3  FIG. 4

DEVICE FOR DISTRACTING VERTEBRAE AND DELIVERING A FLOWABLE MATERIAL INTO A DISC SPACE

FIELD OF THE INVENTION

This invention relates generally to a device for intervertebral disc augmentation, more particularly to a device for distracting vertebral bodies and simultaneously injecting a flowable material into the disc space for augmentation after performing a discectomy or nucleotomy.

BACKGROUND OF THE INVENTION

Spine fusion procedures represent the state of the art treatment for intervertebral disc problems, which generally involve open surgery and the use of interbody fusion cages and spinal fixation systems to stabilize the fusion site. An alternative treatment under evaluation is to replace the disc or nucleus pulposus with a prosthetic device. Examples of some devices currently under investigation include in-situ cured polymers such as polyurethanes and protein polymers, which may have properties varying from a rubbery hydrogel to a rigid plastic. Problems associated with these devices occur during insertion, whereby the pressure required to fill the disc space can cause leakage of the material into sensitive adjacent areas.

A number of devices are available for distracting vertebral bodies or for injecting material into the disc. Some devices are capable of both distraction and injection using the same instrument. These types of devices use a deflated balloon attached to a cannula and inserted between the vertebral bodies. The balloon is inflated with a prosthetic fluid through the cannula to distract the vertebral bodies. This requires high-pressure delivery of the fluid to achieve the pressure needed to distract the vertebral bodies and the balloon and fluid permanently remain in the disc space. Alternatively, a separate device is used to inject the prosthetic fluid around the balloon and the balloon is used strictly for distraction after which it is deflated and removed.

U.S. Pat. No. 4,772,287 ("Ray I") discloses a bladder injected with thixotropic gel implanted between two vertebral bodies to restore the disc height. The technique described requires that the vertebral bodies are first distracted and a bore drilled to allow for insertion of the bladder.

U.S. Pat. No. 5,562,736 ("Ray II") discloses a method for implanting a prosthetic disc nucleus. Ray II teaches cutting a first and second flap in the annulus. The flaps provide access to the nucleus. Ray II then teaches using an inflatable jack to distract the disc space prior to insertion of the prosthetic spinal disc nucleus. The jack has a deflated balloon on its end that is inserted into the nucleus through one of the flaps. The balloon is inflated with fluid causing the vertebral bodies to distract. Once the vertebral bodies are sufficiently distracted the fluid flow is stopped and the prosthetic spinal disc nucleus is inserted through the other flap. The balloon is then deflated and the second prosthetic spinal disc nucleus is inserted. The flaps are closed and placed in contact with the annulus by a suture, staple or glue.

U.S. Pat. No. 6,187,048 ("Milner") discloses an implant for an intervertebral disc nucleus pulposus prosthesis made from a conformable, in-situ curable, material which is resiliently deformable. Milner teaches removing the nucleus material, then either injecting through the annulus or creating an opening in the annulus to deliver a curable material under pressure into the nucleus space. The pressure is necessary to ensure conformation to the nucleus space and/or to increase the internal pressure of the disc space to distract the vertebral bodies. The amount of pressure needed to distract the disc space is high and may allow the material to flow through cracks or voids in the annulus into the disc space. Milner also describes an embodiment where the curable material is injected into a flexible container that is inserted first into the nucleus space in a deflated state and inflated by the material as the material is injected. This method relies on the pressure of the fluid as it is injected to distract the vertebral bodies. Although this avoids the problem of the material leaking through the annulus, it imposes certain constraints such as a designing a cover of the correct shape and size suitable for safe injection of the curable material and prevention of leakage of the material from the cover once filled.

U.S. Pat. No. 6,248,131 ("Felt") describes distracting and injecting at the same time using a balloon device. The balloon can be used as a shell for containing the injected curable biomaterial and also used as a distraction means as the material is injected. Another embodiment describes the balloon as a cylinder shape which when inflated inside the disc space bears against the endplates for the vertebral bodies and distracts them. Then a second device is used to inject the curable biomaterial around the balloon cylinder. The material is allowed to cure and then the balloon is removed and a second curable biomaterial can be injected into the space left where the balloon was. In sum, when Felt discloses injecting material outside of the balloon, Felt discloses using a second device to carry out the injection. Insertion of this second device into the disc should typically require a second breach of the annulus fibrosis.

Therefore, in general, in some embodiments, the art describes free injection of material which may lead to uncontrolled leakage. The art also describes injection of the material into a deflated balloon, which requires leaving the balloon inside the disc space. Lastly, the art describes some of the problems associated with some of these methods include the need for a first instrument to distract the disc space and another to insert or inject the prosthetic fluid. Also, when two devices are used, two incisions in the annulus are required so that distraction and insertion can be accomplished. As noted above, some methods require insertion under high pressure, thereby creating a potential for the prosthetic fluid to ooze or seep out of the disc space intra-operatively.

SUMMARY OF THE INVENTION

The present inventors have developed a device that can be used after performing a discectomy or nucleotomy to both distract the disc space and inject material into the disc space without subjecting the injected material to compressive forces. Because this device provides for the distraction of the vertebral bodies through a means separate from the means for injecting the material, it not only provides a way of delivering a flowable material into the disc space under low pressure, but also allows for the material to cure in-situ without any compressive forces acting upon it. After injection, the device can be removed from the disc space, thereby substantially restoring the nucleus to its original configuration and shape, as well as restoring natural spinal alignment (i.e., natural lordosis or kyphosis).

Therefore, in accordance with the present invention, there is provided a device for distracting two adjacent vertebral bodies defining a disc space therebetween and delivering a flowable material into the disc space, comprising:

a) a body comprising:
  i) a proximal portion,
  ii) a distal portion comprising a shape adapted to distract the disc space, and
  iii) a first longitudinal bore extending through the body and defining a first outlet in the distal portion opening onto the disc space.

Also in accordance with the present invention, there is provided a device for distracting two adjacent vertebral bodies defining a disc space therebetween and delivering a flowable material into the disc space, comprising:
  a) means for distracting the disc space, and
  b) means for delivering a flowable material into the disc space.

Also in accordance with the present invention, there is provided a method for distracting two vertebral bodies and delivering a flowable material into an intervertebral disc space having an outer annulus, comprising the steps of
  a) providing a device for distracting and delivering a flowable material comprising, a body having a proximal portion and a distal portion, the distal portion having a shape adapted to distract, the body also having a longitudinal bore defining a first outlet port in the distal portion, and a first injection port in the proximal portion;
  b) inserting the distal portion of the device through the outer annulus;
  c) distracting the vertebral bodies with the shape; and
  d) introducing the flowable material into the disc space through the injection port.

BRIEF DESCRIPTION OF THE DRAWINGS

These and other features of the invention will be understood from the description below, taken together with the Figures which show illustrative embodiments and several variations and details of construction thereof, wherein:

FIG. 3 shows a top view of an injection of a flowable material into the disc space by the device of FIG. 1.

FIG. 4 shows the withdrawal of the device from the disc space after injection of flowable material into the disc space.

DETAILED DESCRIPTION OF THE INVENTION

For the purposes of the present invention, the "proximal portion" of the body is that portion that penetrates the annulus fibrosis, while the "distal portion" of the body is that portion that remains outside the annulus fibrosis.

The present invention provides a device for distracting (and preferably aligning) two vertebral bodies and delivering a flowable material into the disc space, after a discectomy or nucleotomy has been performed. The present invention simplifies and combines the conventional separate methods of distracting two vertebral bodies and delivering a flowable material into the disc space formed after the removal of the nucleus in a way that allows for the distraction (and preferably spinal alignment) and delivery to be performed by a single device under low pressure.

Figure 1:
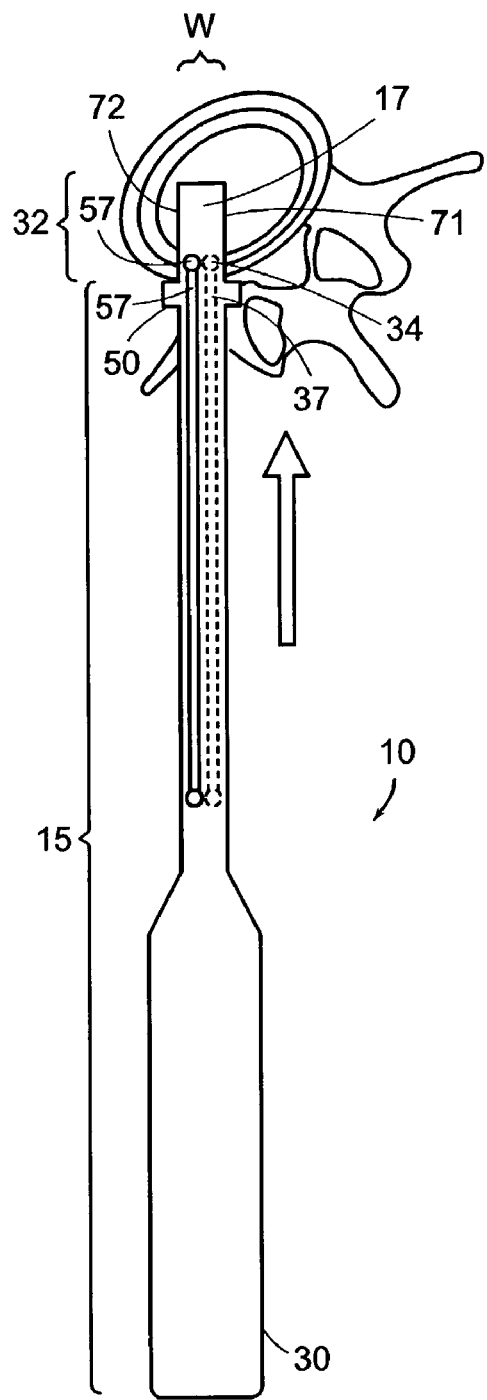
FIG. 1 shows a top view of the device of the present invention inserted into a disc space.
Figure 2:
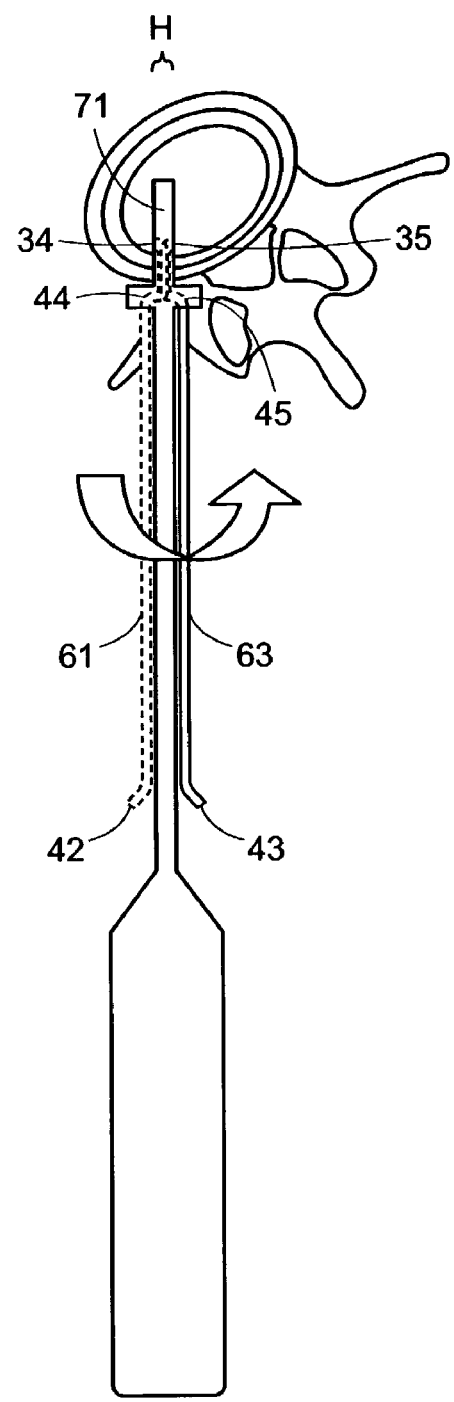
FIG. 2 shows a top view of the device of FIG. 1 inserted into a disc space after rotating the device 90 degrees to distract the disc space.

Now referring to FIGS. 1-2, in preferred embodiments of the invention, there is provided a device 10 for distracting two vertebral bodies and delivering a flowable material into a disc space comprising:
  a) a body 30 comprising:
    i) a proximal portion 15,
    ii) a distal portion 32 comprising a shape 17 adapted to distract the disc space, and
    iii) a first longitudinal bore 37 extending through the body and defining a first outlet 34 in the distal portion opening onto the disc and a first injection port 44.

The device of FIGS. 1-2 further comprises a radially extending flange or stop 50 disposed at the distal most section of the proximal portion of the body.

The shape 17 adapted to distract has a width W is sufficiently large so that, upon rotation, it can sufficiently distract the disc space.

The device of FIGS. 1-2 further comprises a second longitudinal bore 57 extending through the body and defining a second outlet 54 in the distal portion opening onto the disc and a second injection port 45.

The devices of FIGS. 1-2 further comprises first and second tubes 61 and 63, each tube having a proximal open end 42, 43 and a distal open end. In this Figure, each tube runs parallel to the longitudinal axis of the body and enters their respective injection ports 44, 45 of the proximal portion of the body, and terminates within the body at their respective outlets 34, 35. The injection ports accommodate insertion of the tubes such that when flowable material is injected into the proximal open ends of the tubes, it exits through the distal end of the tube and flows into the disc space through the first outlet on the distal portion of the body.

The device of the present invention is typically used immediately after a discectomy or a nucleotomy. In performing the discectomy or a nucleotomy, the surgeon typically makes a small (~5 mm) hole in the annulus fibrosis through which the nucleus pulposus is removed.

In one preferred method of this invention, the surgeon preferably makes a device entry hole in the annulus fibrosis. The device entry hole is typically made by either i) making a second hole in the annulus fibrosis larger than the hole through which the nucleotomy is performed, or ii) enlargening the hole through which the nucleotomy is performed, Next, the surgeon advances the distal end of the device through an incision in the annulus in a first orientation as shown in FIG. 1 until stopped by the stop. Next, now referring to FIG. 2, the surgeon rotates the device 90° C. (as shown by the curved arrow) to a second orientation whereby the desired distraction of the vertebral bodies is achieved. Now referring to FIG. 3, with a syringe 101 attached to injection port 43 by its port 103, the surgeon then delivers through the injection port 44 a flowable material that passes through the body and exits out the outlet port 35 into the disc space. The surgeon allows the material to begin to cure within the disc space to a point where the at least partially cured material can withstand the compressive forces of the spine without leaking into the spinal canal. At this time, and now referring to FIG. 4, the surgeon then removes the device from the patient.

In some embodiments, the distraction and injection are carried out as described above, and then a specified time period is elapsed before the device is withdrawn. This pause allows the injected material to partially cure. The partially cured material is advantageous because it is less susceptible to leak from the annulus fibrosis during withdrawal of the device.

In some embodiments, the withdrawal of the device is a gradual withdraw, wherein flowable material is slowly injected into the void distal of the distal port created by the withdrawal. This gradual withdrawal/injection procedure is advantageous because it allows the surgeon to fill the entire disc space with flowable material. In these embodiments, it is advantageous to use a device in which the outlets are as distal as possible in order to allow the surgeon to continue filling up to the point of withdrawal.

In one preferred use, a first substantially horizontal incision is made in the annulus, the device is inserted into the disc space and rotated, the flowable material is injected into the disc space, a substantially vertical incision Preferably orthogonal to and bisecting the first horizontal incision) is made in the annulus, and the device in its rotated orientation is withdrawn through the substantially vertical incision.

The body of the device of the present invention may have any shape that accommodates a distal portion shaped for distracting and injecting.

In another embodiment of the present invention, the device is integral. In preferred embodiments thereof, the body component of the device is hollow and forms the longitudinal bore, is substantially cylindrically-shaped, and has an injection port within proximal portion for injecting a flowable material and an outlet port within its distal portion from which the flowable material exits into the disc space.

More preferably, the body has a length L and a radius R, wherein the length L is at least ten times the radius R. In these embodiments, the long length of the body allows the surgeon to easily insert the distal portion of the body into the disc space while keeping the proximal end thereof outside the body. Thus, these embodiments are particularly useful in minimally invasive surgeries requiring access through very small incisions.

The device may further comprise a stop mechanism 50 disposed at the distal end of the proximal portion for preventing the body of the device from entering too far into the disc space. The stop mechanism may include a flange extending radially from the body. This stop mechanism allows the surgeon to place the distal portion accurately prior to injecting the flowable material.

The distal portion of the body includes the shape that is adapted to distract the adjacent vertebral bodies and restore spinal alignment.

In some embodiments, the shape adapted to distract is adapted to distract upon insertion into the disc space. Preferably, this shape includes a tapered portion having a maximum height substantially equal to the desired distraction height and a distally decreasing height that allows for easier insertion between the vertebral bodies. Once inserted, the device can be advanced until the desired amount of distraction is reached. In some preferred embodiments, the body has a cylindrical proximal portion, and the distal portion has a symmetric taper (preferably, a bullet).

In another embodiment, the shape adapted to distract is a spreader. In some spreader embodiments, the body has a rectangular cross-section, preferably with rounded outer edges. The distal portion has a height less than the disc space and a width about equal to that of a distracted disc space. In use, the distal portion can be inserted between the vertebral bodies so that the lesser height dimension spans a portion of the disc space, and then rotated 90 degrees so that the bearing surfaces 71, 72 on either side of the greater width dimension bear against the opposing endplates and distract the disc space, to accomplish the necessary amount of distraction.

In some embodiments, the distal portion may be removable from the body. In these embodiments the surgeon leaves the distal portion in the disc space as a spacer and injects a flowable material (like bone cement) around and through the distal portion to secure its position within the disc space.

In some embodiments, the shape adapted to distract has at least one bearing surface having a convex shape adapted to match the contour of the vertebral endplate.

In some embodiments, the shape adapted to distract has a leading edge that is curved to prevent fracture of the endplate.

In some embodiments, the distractor is shaped to provide an anterior-posterior angle to the distracted disc space. In these embodiments, the shape adapted to distract has an upper bearing surface and a lower bearing surface, wherein the upper and lower surfaces define a non-zero angle. In some embodiments, the distal portion of the shape is greater than the proximal portion, and produces a non-zero angle of between about 5 and about 15 degrees. This angle provides lordosis when inserted posteriorly, and kyphosis when inserted anteriorly. In some embodiments, the proximal portion of the shape is greater than the distal potion and produces a non-zero angle of between about −5 and about −15 degrees. This angle provides kyphosis when inserted posteriorly and lordosis when inserted anteriorly.

Figure 5:
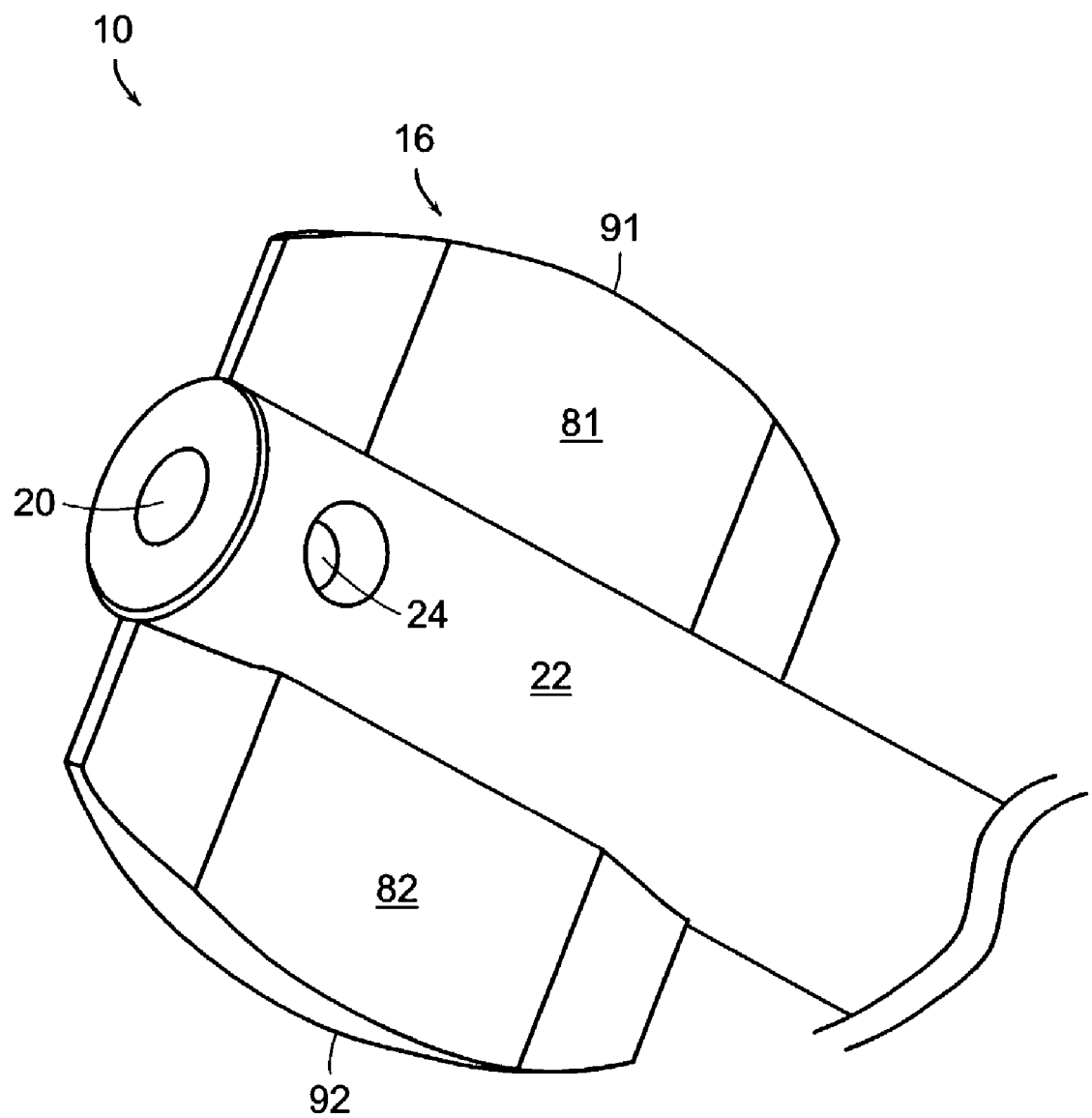
FIG. 5 shows a distal portion of another embodiment of the device of the present invention having an opening at the distal end of the shape adapted for distraction.

Now referring to FIG. 5, in some embodiments, the distal portion has an upper fin 81 extending therefrom, the fin comprising an upper bearing surface 91 having a convex shape. More preferably, the distal portion also has a lower fin 82 extending therefrom, the lower fin comprising lower bearing surface 92 which also has a convex shape, thereby producing a football shaped distal portion. This embodiment is useful when the device is inserted laterally, as the convexity corresponds to the natural contour of the opposing endplates.

In other embodiments, the leading and trailing edges of the fins of FIG. 5 are tapered to facilitate insertion and removal from the disc space.

In some embodiments, the shape adapted to distract is a balloon used purely for distraction purposes i.e., fluid is injected into the disc space through an opening not associated with the balloon). In preferred embodiments thereof, the body comprises:

a) an inflatable balloon having an injection port, b) a first throughbore having a distal portion in fluid connection with the balloon injection port, and c) a second throughbore having a distal portion opening into the disc space.

In preferred uses thereof, the surgeon inserts the distal portion of the body into the disc space, passes a first fluid through the first throughbore to inflate the balloon and thereby distract the disc space, and passes a second fluid through the second throughbore so that the second fluid enters the distracted disc space under low pressure.

In some embodiments, the shape adapted to distract includes upper and lower jaws mounted on a pivot. In use, the shape adapted to distract enters the disc space in a closed position. Then, the surgeon activates the device so that the upper and lower jaws separate from each other to an open position. The outer surfaces of each jaw press against the opposing endplates to provide the desired distraction.

The injection port includes an opening located along the proximal portion of the surface of the body. The flowable material can be injected through this port into the body. There may be more than one injection port located along the proximal portion of the body. The port can include a connection means to an injection device. The material can be injected into the port through any means including syringe and a pump. Preferably, the injection means is a syringe. In some embodiments, the injection means comprises two syringes.

The outlet port includes an opening located on the distal portion of the surface of the body. It allows the flowable material to exit the body and enter into the disc space. In some embodiments, there may be more than one outlet port on the distal portion. The outlet port may be located at the distal end of the body or anywhere along the distal portion of the body.

In some embodiments, as in FIG. 1, the device comprises two distal outlet ports. Preferably, each outlet port opens onto the disc space through a non-bearing surface of the distal portion of the device. This allows the surgeon to fill each side of the disc space when the distractor is in place.

Generally, the more distally disposed the outlet port, the longer the surgeon can continue filling the disc space as the distractor is withdrawn from the disc space. In some embodiments, the device comprises a outlet port opening onto the disc space from the distal half of the distractor component, preferably the distal most quarter of the disc space. Now referring to FIG. 5, the device comprises a outlet port 20 opening onto the disc space from the distal end of the distractor component. This embodiment allows the surgeon to continue filling the disc space until the distractor component is essentially removed from the disc space. The device of FIG. 5 further comprises a outlet port 24 opening onto the disc space from a non-bearing surface 22 within the distal end of the distractor component. A second outlet port (not shown) may be provided opposite of outlet port 24.

The device may be made of materials typically selected for use in surgical instruments. Preferably, the entire device is sterile.

When placed in-situ (and in some instances, after curing), the flowable material preferably replaces as least a portion of the natural function of the nucleus fibrosis. Accordingly, in preferred embodiments, the flowable material is a nucleus pulposus replacement. The flowable materials are preferably selected from the group consisting of liquids, gels (such as hydrogels, such as PVA-based hydrogels), and solid materials that are sufficiently morselized to flow under pressure. Typically, the liquid flowable material cures in-situ. The flowable material may cure in-situ to create a stiff material (such as polyurethane), or a relatively pliant material (such as silicone).

Therefore, in accordance with the present invention, there is provided a kit for providing a nucleus pulposus replacement material, comprising:
  a) device for distracting two adjacent vertebral bodies defining a disc space therebetween and delivering a flowable material into the disc space comprising a body comprising:
    i) a proximal portion,
    ii) a distal portion comprising a shape adapted to distract the disc space, and
    iii) a longitudinal bore extending through the body and defining a first outlet in the distal portion opening onto the disc space, and
  b) a flowable material suitable for use as a nucleus pulposus replacement material.

The present invention relates to a surgical device for distracting two vertebral bodies and delivering a flowable material into the disc space. The invention being thus disclosed and illustrative embodiments depicted herein, further variations and modifications of the invention, will occur to those skilled in the art, and all such variations and modifications are considered to be within the scope of the invention, as defined by the claims appended hereto and equivalents thereof.

What is claimed is:

1. A device for distracting two adjacent vertebral bodies defining a disc space therebetween and delivering a flowable material into the disc space, comprising:
  a) a body comprising:
    i) a proximal portion,
    ii) a distal portion comprising a shape adapted to distract the disc space, wherein the shape adapted to distract has a width and a height, wherein the width is greater than the height, wherein the shape adapted to distract is adapted to distract upon insertion into the disc space and then rotation in the disc space, and wherein the shape adapted to distract has an upper bearing surface and a lower bearing surface, and wherein the upper and lower surfaces define a non-zero angle of between about 5 and about 15 degrees to provide lordosis when inserted posteriorly, and
    iii) a first longitudinal bore extending through the body and defining a first outlet in the distal portion opening onto the disc space, wherein the bore further defines an injection port in the proximal portion of the body, and
  b) an injection device filled with a flowable material selected from the group consisting of an in-situ curable liquid and a gel having a port attached to the injection port.

2. The device of claim 1 wherein the injection device is a syringe.

3. The device of claim 1 wherein the shape adapted to distract is removable.

4. The device of claim 1 further comprising a stop means extending radially from a longitudinal axis of the proximal portion of the body.

5. The device of claim 1 wherein the shape adapted to distract has a convex upper bearing surface.

6. The device of claim 5 wherein the shape adapted to distract has a convex lower bearing surface.

7. The device of claim 1 further comprising:
  c) a tube having an open distal end adapted for insertion in the injection port.

8. The device of claim 1 wherein the body further comprises:
  iv) a second longitudinal bore extending through the body and defining a second outlet in the distal portion opening onto the disc space.

9. The device of claim 1 wherein the first outlet opening onto the disc space is located within a distal half of the shape adapted to distract.

10. The device of claim 1 wherein the first outlet opening onto the disc space is located within a distal quarter of the shape adapted to distract.

11. The device of claim 1 wherein the first outlet opening onto the disc space is located at the distal end of the shape adapted to distractor.

12. A method for distracting two vertebral bodies and delivering a flowable material into an intervertebral disc space having an outer annulus, comprising the steps of
  a) providing a device for distracting and delivering a flowable material comprising, a body having a proximal portion and a distal portion, the distal portion having a shape adapted to distract, wherein the shape adapted to distract has a width and a height, wherein the width is greater than the height, wherein the shape adapted to distract is adapted to distract upon insertion into the disc space and then rotation in the disc space, wherein the shape adapted to distract has an upper bearing surface and a lower bearing surface, and wherein the upper and lower surfaces define a non-zero angle of between about 5 and about 15 degrees to provide lordosis when inserted posteriorly, and the body also having a longitudinal bore defining a first outlet port in the distal portion, and a first injection port in the proximal portion;

b) inserting the distal portion of the device through the outer annulus;

c) distracting the vertebral bodies by rotating the shape; and d) introducing the flowable material into the disc space through the injection port.

13. The method of claim 12 further comprising the step of:

e) removing the device after step d).

14. The method of claim 12 wherein the step of inserting is accomplished through a single incision in the outer annulus.

15. A kit for providing a nucleus pulposus replacement material, comprising:

a) device for distracting two adjacent vertebral bodies defining a disc space therebetween and delivering a flowable material into the disc space comprising a body comprising:
  i) a proximal portion,
  ii) a distal portion comprising a shape adapted to distract the disc space, wherein the shape adapted to distract has a width and a height, wherein the width is greater than the height, wherein the shape adapted to distract is adapted to distract upon insertion into the disc space and then rotation in the disc space, and wherein the shape adapted to distract has an upper bearing surface and a lower bearing surface, and wherein the upper and lower surfaces define a non-zero angle of between about 5 and about 15 degrees to provide lordosis when inserted posteriorly, and iii) a longitudinal bore extending through the body and defining a first outlet in the distal portion opening onto the disc space, and b) a flowable material suitable for use as a nucleus pulposus replacement material, wherein the flowable material is selected from the group consisting of an in-situ curable liquid and a gel.

* * * * *